(12) United States Patent
Sas et al.

(10) Patent No.: US 6,221,417 B1
(45) Date of Patent: Apr. 24, 2001

(54) CONVERSION OF XANTHOPHYLLS IN PLANT MATERIAL FOR USE AS A FOOD COLORANT

(75) Inventors: Benedikt Sas, Turnhout; Clifford Adams, Antwerp, both of (BE)

(73) Assignee: Kemin Industries, Inc., Des Moines, IA (US)

( * ) Notice: Subject to any disclaimer, the term of this patent is extended or adjusted under 35 U.S.C. 154(b) by 0 days.

(21) Appl. No.: 09/193,667

(22) Filed: Nov. 17, 1998

Related U.S. Application Data (63) Continuation of application No. 08/856,357, filed on May 14, 1997, now Pat. No. 5,876,782.

(51) Int. Cl.$^7$ .................................. A23L 1/27; C12C 5/04

(52) U.S. Cl. ................... 426/540; 426/541; 426/544; 426/262; 426/270; 8/438; 8/646

(58) Field of Search ........................................ 426/262, 270, 426/540, 541, 544; 8/438, 646

(56) References Cited

U.S. PATENT DOCUMENTS

| | | |
|---|---|---|
| 3,998,753 | 12/1976 | Antoshkiw et al. . |
| 4,048,203 | 9/1977 | Philip . |
| 4,316,917 | 2/1982 | Antoshkiw et al. . |
| 4,522,743 | 6/1985 | Horn et al. . |
| 5,084,292 | 1/1992 | Van Dort et al. . |
| 5,180,747 | 1/1993 | Matsuda et al. . |
| 5,536,504 | 7/1996 | Eugster et al. . |
| 5,648,564 * | 7/1997 | Ausich et al. ................ 568/834 |

FOREIGN PATENT DOCUMENTS

| | | |
|---|---|---|
| 82133160 | 11/1982 | (JP) . |
| 82180663 | 1/1983 | (JP) . |
| 83173164 | 1/1984 | (JP) . |

\* cited by examiner

Primary Examiner—Nina Bhat
(74) Attorney, Agent, or Firm—Kent A. Herink, Esq.; Davis, Brown, Koehn, Shors & Roberts, P.C.

(57) ABSTRACT

This invention relates to the in situ process for converting non-free-form xanthophylls to free xanthophylls in the biological material of the plant. The method, more particularly, relates to a method that would liberate xanthophylls by transesterification of acyl-xanthophylls in plant materials which is used as a natural food colorant.

4 Claims, 6 Drawing Sheets

Figure 6

CONVERSION OF XANTHOPHYLLS IN PLANT MATERIAL FOR USE AS A FOOD COLORANT

CROSS REFERENCES RELATED TO APPLICATION

This is a continuation of application Ser. No. 08/856,357, filed May 14, 1997, now U.S. Pat. No. 5,876,782.

FIELD OF THE INVENTION

This invention relates to the in situ process for converting non-free-form xanthophylls to free xanthophylls in the biological material of the plant. The method, more particularly, relates to a method that would liberate xanthophylls by transesterification of acyl-xanthophylls in plant materials.

BACKGROUND OF THE INVENTION

Carotenoids, are a group of red and yellow pigments contained in plants and fruits. Carotenoids include carotenes and hydroxylated carotenoids designated xanthophylls. Xanthophylls include lutein, zeaxanthin, capsorubin, capsanthin, astaxanthin, and canthaxanthin.

The animal feed industry, the food industry, and the pharmaceutical industry have all indicated a strong interest in xanthophylls. The poultry industry receives a benefit in adding the xanthophylls to enhance the yolk color of eggs. The pharmaceutical companies have found that xanthophylls are useful in certain tumor treatments and as an antioxidant. The food industry has found that consumers are looking for naturally-occurring food colorants. Annatto, saffron, and paprika are a few natural carotenoids that have traditionally been used for food coloring. The dramatic red and yellow coloration and the xanthophylls' natural occurrence in edible plants such as green vegetables and fruit, for example, broccoli, green beans, peas, brussels sprouts, cabbage, kale, spinach, kiwi, and honeydew, have led to many uses, including a pigmentation additive for animal feeds. In certain vegetables, the xanthophylls are in the free non-esterified form. However, the large quantities of chlorophylls in green vegetables makes concentration or extraction of the xanthophylls difficult. A number of xanthophylls are also present in yellow-colored fruits and vegetables, such as mangoes, peaches, prunes, acorn squash, and oranges. These contain fewer chlorophylls, but often the xanthophylls exist in the esterified form with fatty acids such as myristic, lauric, and palmitic acids. Thus, to be metabolized in a feed additive, the xanthophylls' ester must undergo conversion to the free xanthophylls which is then metabolizable by the organism.

Although these various plant materials contain xanthophylls, the desired xanthophylls will drive the selection of the material used. For example, it is well known to use the petals of the marigold flower, *Tagetes erecta,* for the extraction of the lutein xanthophylls. Marigolds are readily cultivated and have been used as a pigment source for poultry. Lutein occurs in the marigold flower, diacylated with palmitic and myristic acids in long, fatty acid esters, typically as diesters in the chromoplastids.

The animal feed industry has taken two different approaches to providing xanthophylls in animal feeds, particularly lutein to poultry feeds. The industry had used the dried marigold meal as a feed additive, thus providing the lutein in the less useable acylated form. This form of the xanthophylls requires more consumption of the marigold meal to get the pigment desired. Alternatively, the industry has used a number of processes, starting with the extraction of the xanthophylls from the plant material and the formation of oleoresins. The industry then goes further and processes the oleoresins to convert the xanthophylls from the acylated form to the free form by a number of different processes, including transesterification for some oleoresin processing of paprika, though for lutein the process is primarily by saponification. The converted oleoresin requires less consumption by the animal to get the desired xanthophylls. However, formation of oleoresins and the processing thereof by saponification is both time-consuming and adds labor costs to the feed product.

Saponification is the conversion of the fatty acid into a soap by treating it with an alkali. The saponification number is the number of milligrams of potassium hydroxide required to saponify one gram of the ester. After saponification, the industry has often used solvents to crystallize the lutein from the oleoresin. This has made the xanthophylls more purified and available to the organism consuming the lutein, but it has added time and labor to the process of supplying the xanthophylls to the feed mixture.

Some of the following patents indicate the processes for recovering various compounds such as xanthophylls from oleoresins. U.S. Pat. No. 5,602,286 describes a process for recovering xanthophylls from corn gluten. The patent has the steps of adding ethanol as an extraction step, filtering, stripping to form the crude xanthophyll, and then using ethanol, using KOH as the sponification step, washing and filtering, then purifying to the refined xanthophylls.

Three Japanese references also show the use of similar oleoresin extractions. No. 82,133,160 Japan (1982) shows a red pepper pigment production using a red pepper oleoresin, in either water or alcohol-mixtures, treated with KOH, NaOH, $CaCO_3$, and then treated with acids such as HCl, $H_2SO_4$, $H_3PO_4$, HOAc, lactic and citric acids. The pigment solutions are removed with organic solvents such as MeOH, EtOH, PrOH and acetone.

Patent No. 82,180,663 (1982), shows paprika food coloring agents that are extracted as an oleoresin. The oleoresin is heated with basic alkali metal compounds such as KOH, NaOH, $K_2CO_3$, $Na_2CO_3$, or sodium alcoholate, and mixed with one or more hydroxides, carbonates, or alkali earth metals, such as $Ca(OH)_2$. The precipitates are extracted with organic solvents and yield an odorless oleoresin pigment. Patent No. 83,173,164 shows paprika pigments can be prepared by treating paprika oleoresin with alkali at temperatures below 50° C. in the presence of halogen ions, sulfates, bicarbonate, carbonate, phosphate, and aliphatic carboxy ions, then treated with an organic solvent, and, finally, extracted with acetone.

The U.S. Pat. No. 5,382,714 describes a method of producing substantially pure lutein. In this patent, the starting material was marigold petals. The process of saponification of the petals is briefly described in column 5, example 1. The flower petals were tested for herbicides and pesticides and then the xanthophyll-containing material was subjected to saponification with aqueous potassium hydroxide. This was accomplished by continuous mixing under heat (65–70° C.) of food grade potassium hydroxide 45%. This accomplished the conversion of 98% of lutein into a form which was free of fatty acids and present as a yellow oil. This material could then be used as a feed or food additive.

The present invention provides a method of in situ conversion of the xanthophylls into the free form by liberation of the xanthophylls by transesterification; thus avoiding the need for the formation of the oleoresin. This oleoresin conversion requires an organic solvent extraction of the plant material; hexane is often used. The present invention provides in situ free-form xanthophylls by transesterification of in situ material, thus eliminating the need for an oleoresin or saponification of the material. The present invention allows the marigold meal to be subjected to transesterification and then used, without the extraction of the xanthophylls from the meal.

SUMMARY OF THE INVENTION

It is evident that there is a need to convert acylated xanthophylls in plant material to the free form.

The objective of this invention is to fulfill that need.

Another object of my invention is to provide a marigold meal that has a high free lutein content.

Yet another object of my invention is to provide a marigold meal as a feed additive that, in fact, provides additional pigment to eggs, when compared to the same marigold meal as a feed additive that has not undergone the treatment of the present invention.

Another additional objective of my invention is to provide plant material which contains a substantially greater percentage of the free form of xanthophylls than contained in the original plant material prior to liberation.

Broadly, then, the present invention includes an improved plant material made from a natural plant material containing at least some non-free-form xanthophylls, comprising plant materials containing in situ, less of the non-free form xanthophylls, and more of the free-form xanthophylls, wherein the free form of xanthophylls in situ in the improved plant material has increased beyond the amount in the natural plant material.

The invention can have a number of different plant materials, including flowers and the petals of flowers. A flower of particular usefulness is *Tagetes erecta*. This type of flower is useful if the desired xanthophylls are lutein. The bulk of the xanthophylls in marigolds exist in nature in the form of non-free-form xanthophylls, as fatty acid esters. The present invention is adapted to convert the non-free xanthophylls into their free form. When the marigold flowers are employed, this conversion by transesterification produces a nonacylated lutein. The present invention can improve plant material so that it contains at least 5% more free-form xanthophylls than does the natural plant material in situ.

Another embodiment of the present invention is an improved animal feed composition comprising: vitamin and minerals, along with a source of carbohydrates selected from the group consisting of soybean, peanuts, corn, alfalfa, wheat, and barley, and improved plant material containing in situ more free-form xanthophylls than the natural in situ amount of xanthophylls in the plant material from which the improved plant material was formed, wherein the xanthophylls are more bioavailable to an animal fed the animal feed.

This feed can contain improved plant material in the form of flowers. If the desired xanthophyll is lutein, then said flowers are marigolds. If the desired xanthophyll is capsanthin, then paprika can be used.

This animal feed is designed for the nutritional requirements of poultry, wherein the xanthophyll acts as a pigmenter for the animal products, such as eggs and meat.

The present invention is believed to be particularly useful for chickens. Certain xanthophylls could also be useful in swine feed to color the meat or other animal byproducts.

A feed for poultry is preferably characterized by having the animal feed evidencing the bioavailability of the free-form xanthophylls by having increased pigmentation from the consumption of said free form xanthophylls, especially when the fed xanthophylls are lutein.

The present invention does not only encompass a product, but also, the method of forming the free-form xanthophylls. Thus, broadly, the present invention covers a method of improved plant material made from a natural plant material containing at least some non-free-form xanthophylls, comprising the steps of treating said natural plant material in situ with a solvent; adding a base capable of transesterification of non-free-form xanthophylls to the free-form xanthophylls; neutralizing the reaction, forming the improved plant material having more free-form xanthophylls than the natural plant material. The method can also include the step of drying the improved plant materials to remove any solvent.

The method of the present invention includes using plant material such as flowers. If the desired product is lutein, then flowers such as *Tagetes erecta* can be used.

The method uses a solvent in the reaction. The solvent can be, broadly, an alcohol and, more preferred, an alkanol or alkenol. If an alcohol is used, the alcohol preferably has one to four carbons.

The alcohol is selected from the group consisting of methanol, ethanol, isopropyl alcohol, butanol and the like. The method of the present invention uses a base. The base can be selected from the group consisting of potassium hydroxide, potassium sorbate, NaOMe, animal liver lipase, yeast lipase, NaOEt, KOMe, KOEt, $Na_2CO_3$, $K_2CO_3$, and the like.

The method also includes the step of stopping the reaction by neutralizing the reaction with a Lewis acid. The preferred Lewis acid is phosphoric acid. However, the Lewis acid can be selected from the group consisting of HCl, $NH_4Cl$, sulfuric acid, acetic acid, $AlCl_3$, and the like.

The method does not require an extractor, such as petroleum ether, hexane, or a number of other known extractors, to remove the xanthophyll from the plant material.

The method can have plant material such as flowers, roots, or fruit, but preferably without chlorophyll in the product.

DETAILED DESCRIPTION OF THE INVENTION

This invention relates to the in situ process for converting non-free-form xanthophylls to free xanthophylls in the biological material of the plant. The method, more particularly, relates to a method that would liberate xanthophylls by transesterification of acyl-xanthophylls in plant materials, and result in improved plant material having more free-form xanthophyll than the original plant material from which it was made.

Thus, the present invention provide a method of liberating xanthophylls in situ in plant, vegetable, or fruit material. A xanthophyll in the free form, such as lutein, zeaxanthin or capsanthin, is formed from the xanthophyll diester in the plant material. The plant material should have relatively concentrated amounts of the desired xanthophyll in the non-free form, which is usually, and preferably, the form of a fatty acid ester. Marigolds are an excellent source of lutein in the form of diesters presently known in nature. The wolfberry fruit (*Lycium barbarum*) is an excellent source of zeaxanthin diesters, and the pepper plant (*Capsicum annum*) has capsanthin in the form of diesters. Other plants, fruits and vegetables having high concentrations of desired xanthophylls can also be utilized.

The term non-free-form xanthophyll refers to a xanthophyll that is in a form that can be transesterified to the free form of the xanthophyll.

The term free-form xanthophyll refers to a xanthophyll which is not in an esterified form.

The term bioavailability refers to the extent to which the xanthophyll is available to the body of the organism consuming it.

The term base refers to potassium hydroxide, potassium sorbate, NaOMe, animal liver lipase, NaOEt, KOMe, KOEt, $Na_2CO_3$, $K_2CO_3$, and such other non-nucleophilic and non-strong kinetically deprotonating material which does not cause kinetic deprotonation in the alpha-position of the carbonyls or highly conjugated double bond systems; for example, LDA or BuLi would be excluded from the definition of base, because these chemicals cause deprotonation in the alpha-position of the carbonyls and highly conjugated double bond systems.

The term ratio of base to plant material (meal) by weight refers to the amount of base used in the reaction compared to the weight of the plant material. This amount is determined by the pH of the reaction and the desired reaction times. The preferred pH is between 11–14; lower pH can be used, but it increases the reaction time.

The term solvent refers to a chemical in which the transesterification of the xanthophyll can be carried out; the chemical preferably has a hydroxyl group. The solvent is preferably an alcohol with 1–4 carbons. More preferably, the solvent is selected to have a boiling point that allows the reaction temperature of the transesterification to be kept at 75–85° C., such as MeOH.

Plant material refers to plants containing xanthophylls in the non-free form of the xanthophyll.

The contemplated plant sources contain xanthophylls in the esterified form as a mono- or di-$C_{12}$–$C_{18}$ long-chain fatty acid, such as lauric, myristic, oleic, linolenic and palmitic acids. Marigolds are an excellent source of lutein in the form of diesters presently known in nature, the wolfberry fruit (*Lycium barbarum*) is an excellent source of zeaxanthin diesters; and the pepper plant (*Capsicum annum*) has capsanthin in the form of diesters. Other plants, fruits, and vegetables having high concentrations of desired xanthophylls can also be utilized. The use of flowers and roots and fruits often avoid the difficulty of separation of the free form of the xanthophylls from the other pigments such as chlorophyll if the xanthophyll is to be extracted.

It is well known in the art to extract carotenoids from plants. It is equally well known in the art that marigold meal and certain other plant materials can be fed to animals as a feed additive to cause pigmentation of the animal products such as eggs or meat. Marigold meal has be supplied to pigment chicken eggs for a long period of time. Lutein has been extracted from marigold for its pigmentation properties. The prior art has taught and suggested that there are two ways to supply lutein. One is as the naturally-occurring plant material with the lutein in the non-free form; alternatively, the lutein can be extracted by forming an oleoresin, saponifying the oleoresin, and supplying the saponified material having the free form of the xanthophyll. The present invention provides a new and better alternative to these—a method of supplying in situ an increased amount of free-formed xanthophylls in situ in the plant material without having to form the oleoresin.

The prior art teaches that organic extractors have been used to extract carotenoids from plant material and form the oleoresins. Hexane, acetone, petroleum ether, methanol, ethyl acetate, diethyl either, heptanes, chloroform, and tetrahydrofuran have been used as the organic extractors. These extractors result in what is called an oleoresin, which contains diesters. The prior art then teaches the use of a saponification reaction that cleaves the fatty acids from the xanthophyll diesters. There are a number of known methods for the saponification. These produce free-form xanthophylls along with soaps of the fatty acids. The soaps are made with alkali solutions, such as potassium hydroxide and sodium hydroxide, in an aqueous solution. Even though similar chemicals may be used in the saponification process, clearly, the present invention does not require the organic extraction step, nor the saponification step, to provide an improved plant material.

The liberation of xanthophylls in situ in plant material proceeds by the following chemical equation:

-continued

Clearly, the diacyl-xanthophylls are converted by transesterification into free xanthophylls in situ (in the crude plant material). This process avoids the cost, processes, and potentially hazardous chemicals associated with the production of an oleoresin. Additionally, the plant material can act as the carrier material further increasing the efficiency of the process.

Thus, the steps of the present method include placing the plant material containing the non-free form of xanthophylls in the solvent and base. The ratio of base to plant material (meal) by weight is the amount of base used in the reaction compared to the weight of the plant material. This amount is determined by the pH of the reaction and the desired reaction times. The preferred pH is between 11–14; lower pH increases the reaction time.

For approximately every 32 grams of xanthophyll activity in the raw plant material, approximately 770 g of base, such as KOH, was placed in 11 liters of the solvent. The solution containing the plant material was kept at a pH of approximately 13; between 11–14 were acceptable levels, with 13 being the preferred level. The reacting solution was stirred until complete conversion was observed. The run time was approximately 10 hours at 69° C., and was monitored by HPLC.

The reaction solution was neutralized to a pH of 7 with phosphoric acid. Any number of neutralizing acids and agents could be employed, but phosphoric acid is preferred. The solvent, preferably an alcohol and more preferably MeOH, was removed with 16 hours of distillation at 69° C. The temperature of distillation can be higher or lower, as long as it is above the boiling point of MeOH and the distillation is done in a commercially-reasonable time.

Other carriers can be added to the plant residue material, such as almond shell meal, silicates, and the like. The residue is dried after the distillation of the solvent, either at room temperature at one atm or by vacuum-drying in an oven at a temperature <50° C. The method of drying is a question of drying time and is not critical. The plant residue material which now has in situ free-form xanthophylls therein is mixed, and a fine powder with a xanthophyll activity of 10–14 g/kg is achieved. The final product is preferably stored at room temperature under nitrogen.

The following bases can also be used in the present invention. Their selection can be based on the economics of the process, the speed of the process, and the acceptability trace amounts of the components. The present invention, a plant material having free-form xanthophylls, can be marigold meal that has been converted. The converted marigold meal was fed to poultry along with a control (the same marigold meal from the same batch of plant materials) to the same type and age of egg-laying hens. The data indicates that there was increased use of the xanthophylls in the converted meal. In other words, there was more pigmentation of the yolks of the egg when the same amount of converted plant material was consumed compared to the non-converted plant material. Thus, the process is providing the xanthophylls in a more bioavailable form to the animal consuming the product. Generally, this test was run with marigold meal that was processed by the steps as listed below to provide in situ free-form xanthophylls.

EXPERIMENT 1

LIBERATION OF LUTEIN BY MEANS OF TRANSESTERIFICATION

Step 1 Marigold meal (2 kg with a total xanthophyll activity of 16 g/kg) in MeOH/KOH (11 L/770 g, pH=13) was stirred until complete conversion was observed (approx. 10 hours) at 69° C. The reaction turnover was monitored by HPLC. See FIG. 1 and FIG. 3.

Step 2 The reaction mixture was neutralized (pH=7) with phosphoric acid and MeOH was removed by distillation at 69° C. (distillation time=approx. 16 hours).

Step 3 The residue was then dried in a well-ventilated room at room temperature and at 1 atm or by means of vacuum drying in an oven (temperature <50° C.).

Step 4 After mixing and blending, a fine powder was obtained with a total xanthophyll activity of 10 to 14 g/kg (depending on the duration of the reaction and drying process). The final product is stored at room temperature under nitrogen.

The process described above can use a number of differing bases that include, but are not limited to, potassium hydroxide, potassium sorbate, NaOMe, animal liver lipase, NaOEt, KOMe, KOEt, $Na_2CO_3$, $K_2CO_3$, and such other non-nucleophilic and non-strong kinetically deprotonating materials which do not cause deprotonation in the alpha-position of the carbonyls and highly conjugated double bond systems. The preferred base is KOH, due to its availability at an inexpensive price and its effectiveness in avoiding the issues of deprotonation. The amounts to use of another base is readily determined.

As will be noted, the process described in the following experiments does not involve the use of an aqueous solution. Instead, the solvent is an alcohol solvent that, further along in the process, is removable by distillation. MeOH is preferred as a solvent, but other types of alcohol, such as isopropyl alcohol, ethanol, butanol, and the like can be employed without undue experimentation by the ordinarily skilled person in the art. The solvent, clearly, is a chemical in which the transesterification of the xanthophyll can be carried out without interfering with the chemical process of transesterification; the solvent, preferably, has a hydroxyl group and is not an aqueous solution.

The neutralizing agent is preferably phosphoric acid. But as a neutralizing acid, other Lewis acids, such as HCl, sulfuric acid, $AlCl_3$, $NH_4Cl$, acetic acid, and the like can be used.

Plant material refers to plants containing xanthophylls in the non-free form.

The contemplated plant source contain xanthophylls in the esterified form as a mono- or di-$C_{12}$–$C_{18}$ long-chain fatty acid such as lauric, myristic, oleic, linolenic, and palmitic acids. Xanthophylls are found in a number of differing plant materials. Marigold have lutein, and paprika has capsanthin. This process works to liberate a number of non-free-form xanthophylls in plant materials.

The experiment below is the reaction procedure for the liberation of capsanthin in paprika meal.

EXPERIMENT 2

LIBERATION OF BY MEANS OF TRANSESTERIFICATION OF PAPRIKA TO FORM FREE CAPSANTHIN

Paprika plant material having a determined total xanthophyll activity per kg is placed in MeOH (11 L, without ethoxyquin) and is stirred for 8 hours at 69° C. and for 12 hours at room temperature with KOH (770 g, pH=13). The reaction turnover is monitored by HPLC. The reaction mixture is neutralized (pH=7) with phosphoric acid. MeOH (6 L) is removed by distillation at 69° C. (distillation time=16 hours at 69° C. with a pause of 48 hours at room temperature). The residue is then dried on standing at room temperature at 1 atm, and is followed by vacuum drying in an oven (50° C., 100 Torr) for 2 hours. After mixing, a fine powder is obtained with a total xanthophyll activity to be determined per kg (depending on the duration of the drying process and efficacy of the mixing).

ANALYSIS

Can be performed with the following parameters:
Monitoring the transesterification:
Chrompack chromsep 100*46 mm (L*ID)
15018 microspher C18 cat. no. 28076
flow 1 ml/min eluent: $CH_2Cl_2/CH_3CN$ 30/70 scanning at 450 nm Measuring the total xanthophyll activity was performed by means of a spectrophotometer.

EXPERIMENT 3

CHROMATOGRAPHY COMPARISON OF MARIGOLD MEAL WITH TRANSESTERIFIED MARIGOLD MEAL TO EVALUATE THE FREE LUTEIN

Figure 1:
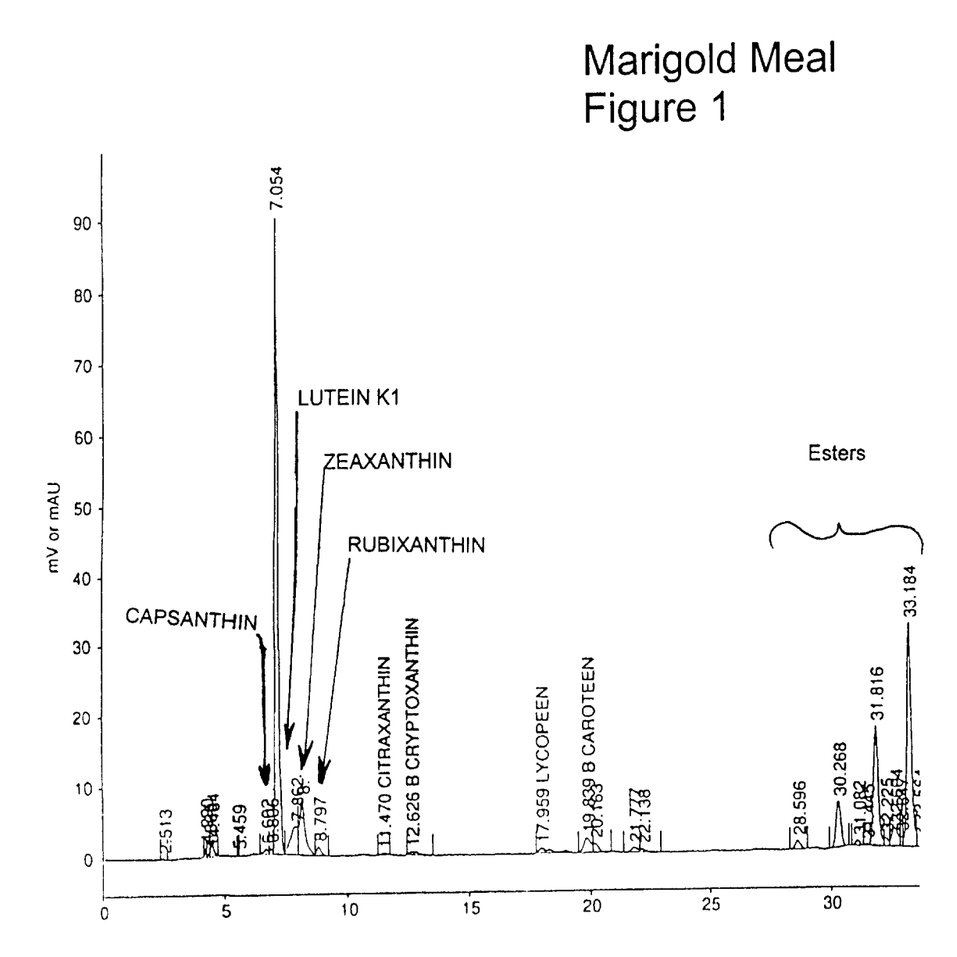
FIG. 1 is the chromatogram of untreated marigold meal.
Figure 3:
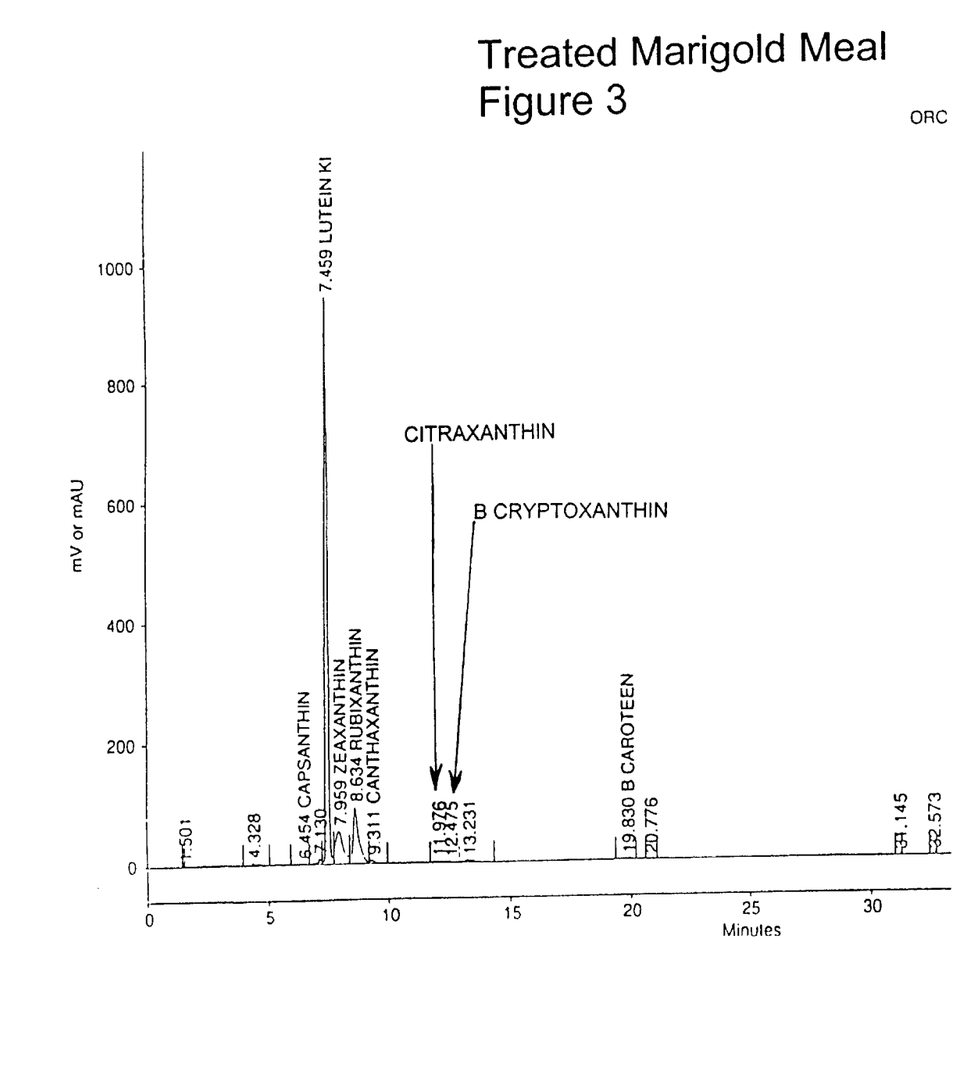
FIG. 3 is the chromatogram of conversion to free form of lutein from treated marigold meal.

The transesterification process described above in EXPERIMENT 1 was employed on one of the marigold meal samples; the other sample was not treated by the transesterification process. The two materials (the plant material that had been treated and the untreated material) was analyzed, and the results are shown in FIGS. 1 and 3. FIG. 1 shows the untreated marigold meal, and FIG. 3 shows the treated marigold meal. FIG. 3 as subjected to the following conditions:

Column Pressure (psi): 1866 Column Temperature (°C.): N/A

Noise (microAU): 3e+001 Drift (microAU/min): 3e+001

The untreated marigold meal had the following parameters and conditions:

Column Pressure (psi): 2391 Column Temperature (°C.): N/A

Noise (microAU): 4e+001 Drift (microAU/min): 1e+001

The graph in FIG. 1 shows that the lutein of the marigold meal has a lot of ester activity in the 28–33 range, and a lutein level in the 7–8 range. The transesterified marigold meal shows that the lutein peak is still high, and the esters in the 31–33 area no longer exist.

The following data was gathered from the marigold meal and FIG. 1.

| Component | RT (min) | Area | Height | Area % | Peak Type |
|---|---|---|---|---|---|
| Unident0001 | 2.513 | 1110 | 194 | 0.05 | Resolved |
| Unident0002 | 4.220 | 4408 | 1331 | 0.19 | Fused |
| Unident0003 | 4.365 | 2763 | 670 | 0.12 | Fused |
| Unident0004 | 4.484 | 17210 | 2068 | 0.76 | Fused |
| CAPSANTHIN | 6.602 | 8032 | 758 | 0.35 | Fused |
| Unident0007 | 6.805 | 6003 | 891 | 0.26 | Fused |
| Unident0008 | 7.054 | 794979 | 90124 | 34.96 | Fused |
| LUTEIN K1 | 7.862 | 85277 | 3973 | 3.75 | Fused |
| ZEAXANTHIN | 8.110 | 123244 | 7773 | 5.42 | Fused |
| RUBIXANTHIN | 8.797 | 15407 | 1288 | 0.68 | Fused |
| CANTHAXANTHIN | 9.900 | 0 | 0 | 0 | NF |
| CITRAXANTHIN | 11.470 | 3141 | 223 | 0.14 | Resolved |
| B CRYPTOXANTHIN | 12.626 | 8967 | 478 | 0.39 | Resolved |
| LYCOPEEN | 17.959 | 27086 | 689 | 1.19 | Fused |
| B CAROTENE | 19.839 | 41511 | 2125 | 1.83 | Fused |
| Unident0017 | 20.163 | 17368 | 1290 | 0.76 | Fused |
| Unident0018 | 21.777 | 12620 | 719 | 0.55 | Fused |
| Unident0019 | 22.138 | 6278 | 502 | 0.28 | Fused |
| Unident0020 | 28.596 | 16349 | 1191 | 0.72 | Resolved |
| Unident0021 | 30.268 | 92474 | 6473 | 4.07 | Fused |
| Unident0022 | 31.082 | 9061 | 802 | 0.40 | Fused |
| Unident0023 | 31.445 | 2991 | 321 | 0.13 | Fused |
| Unident0024 | 31.816 | 228688 | 16904 | 10.06 | Fused |
| Unident0025 | 32.225 | 13487 | 1254 | 0.59 | Fused |
| Unident0026 | 32.604 | 45440 | 2610 | 2.00 | Fused |
| Unident0027 | 32.847 | 10055 | 1418 | 0.44 | Fused |
| Unident0028 | 33.184 | 408509 | 31639 | 17.96 | Fused |
| Unident0029 | 33.564 | 31417 | 2652 | 1.38 | Fused |
| Unident0030 | 33.940 | 79024 | 4915 | 3.48 | Fused |
| Unident0031 | 34.533 | 161146 | 8099 | 7.09 | Fused |
| Totals | | 2274045 | 193374 | 100.00 | |

-continued

| Component | RT (min) | Area | Height | Area % | Peak Type |
|---|---|---|---|---|---|
| Unident0002 | 4.328 | 57885 | 4754 | 0.54 | Resolved |
| CAPSANTHIN | 6.454 | 17237 | 901 | 0.16 | Fused |
| Unident0004 | 7.130 | 94538 | 8757 | 0.88 | Fused |
| LUTEIN K1 | 7.459 | 7571877 | 942410 | 70.17 | Fused |
| ZEAXANTHIN | 7.959 | 1247667 | 54701 | 11.56 | Fused |
| RUBIXANTHIN | 8.634 | 1533918 | 92877 | 14.21 | Fused |
| CANTHAXANTHIN | 9.311 | 72773 | 5608 | 0.67 | Fused |
| CITRAXANTHIN | 11.976 | 51048 | 1889 | 0.47 | Fused |
| B CRYPTOXANTHIN | 12.475 | 9046 | 880 | 0.08 | Fused |
| Unident0011 | 13.231 | 87645 | 3194 | 0.81 | Fused |
| LYCOPEEN | 16.350 | 0 | 0 | 0 | NF |
| B CAROTEEN | 19.830 | 28395 | 1187 | 0.26 | Resolved |
| Unident0014 | 20.776 | 5077 | 454 | 0.05 | Resolved |
| Unident0015 | 31.145 | 2061 | 238 | 0.02 | Resolved |
| Unident0016 | 32.573 | 3773 | 477 | 0.03 | Resolved |
| Unident0017 | 33.801 | 8411 | 754 | 0.08 | Resolved |
| Totals | | 10791351 | 1119081 | 100.00 | |

EXPERIMENT 4

CHROMATOGRAPHY COMPARISON OF PAPRIKA WITH TRANSESTERIFIED PAPRIKA TO EVALUATE THE FREE CAPSANTHIN

Figure 2:
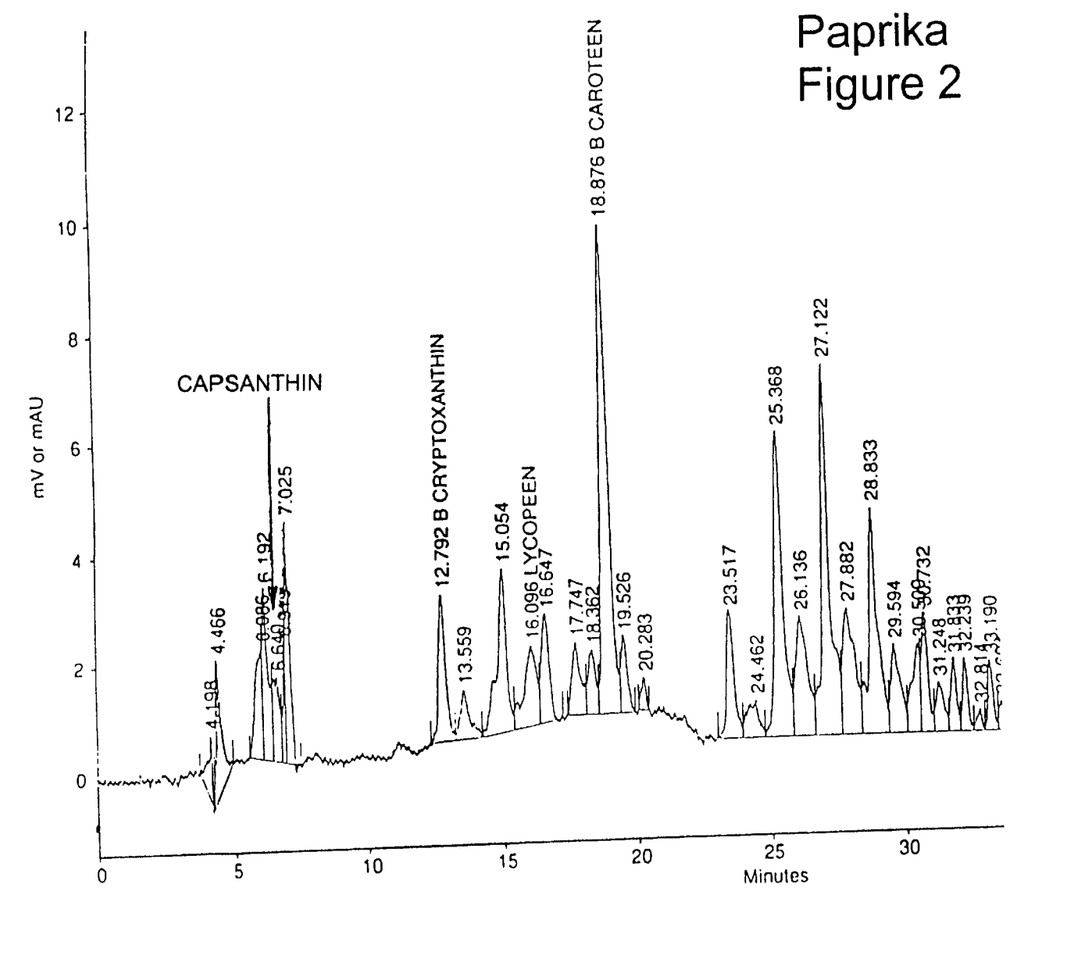
FIG. 2 is the chromatogram of untreated paprika.
Figure 4:
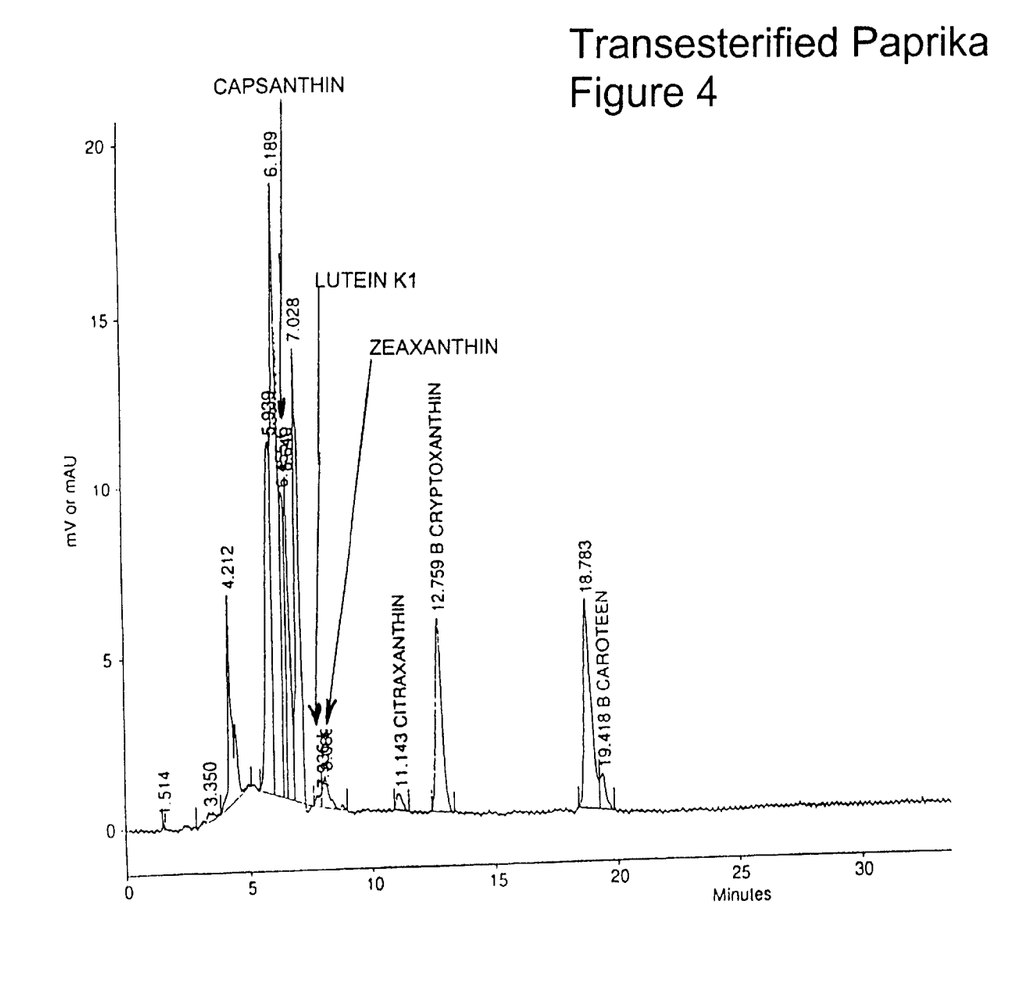
FIG. 4 is the chromatogram of conversion to free form of capsanthin from treated paprika.

The transesterification process described above in EXPERIMENT 3 was employed on one of the paprika samples; the other sample was not treated by the transesterification process. The two plant materials, the treated and untreated material, was analyzed, and the results are shown in FIGS. 2 and 4. FIG. 2 shows the untreated paprika, and FIG. 4 shows the treated paprika. Treated paprika in FIG. 4 was subjected to the following conditions and gave the following data.

Transesterified Paprika

Acquisition Log

Column Pressure (psi): 1799 Column Temperature (°C.): N/A

Noise (microAU): 5e+001 Drift (microAU/min): 1e+002

| Component | RT (min) | Area | Height | Area % | Peak Type |
|---|---|---|---|---|---|
| Unident0002 | 3.350 | 5402 | 305 | 0.46 | Fused |
| Unident0003 | 42.12 | 75241 | 6091 | 6.47 | Fused |
| Unident0004 | 5.939 | 167992 | 10409 | 14.44 | Fused |
| Unident0005 | 6.189 | 293468 | 17946 | 25.22 | Fused |
| CAPSANTHIN | 6.455 | 89525 | 8942 | 7.69 | Fused |
| Unident0007 | 6.640 | 93922 | 9488 | 8.07 | Fused |
| Unident0008 | 7.028 | 163104 | 13380 | 14.02 | Fused |
| LUTEIN K1 | 7.936 | 4794 | 380 | 0.41 | Fused |
| ZEAXANTHIN | 8.088 | 17197 | 921 | 1.48 | Fused |
| RUBIXANTHIN | 8.550 | 0 | 0 | 0 | NF |
| CANTHAXANTHIN | 9.900 | 0 | 0 | 0 | NF |
| CITRAXANTHIN | 11.143 | 7630 | 481 | 0.66 | Resolved |
| B CRYPTOXANTHIN | 12.759 | 100344 | 5656 | 8.62 | Resolved |
| LYCOPEEN | 16.350 | 0 | 0 | 0 | NF |
| Unident0016 | 18.783 | 129299 | 6123 | 11.11 | Fused |
| B CAROTENE | 19.418 | 15731 | 1033 | 1.35 | Fused |
| Totals | | 1163652 | 81155 | 100.00 | |

FIG. 2 was subjected to the following conditions and gave the following data.

Non-transesterified Paprika

Acquisition Log

Column Pressure (psi): 1810 Column Temperature (°C.): N/A

Noise (microAU): 3e+001 Drift (microAU/min): 3e+001

| Component | RT (min) | Area | Height | Area % | Peak Type |
| --- | --- | --- | --- | --- | --- |
| Unident0001 | 4.198 | 12917 | 1238 | 0.88 | Fused |
| Unident0002 | 4.466 | 31213 | 2498 | 2.12 | Fused |
| Unident0003 | 6.086 | 36925 | 2042 | 2.51 | Fused |
| Unident0004 | 6.192 | 43531 | 3157 | 2.96 | Fused |
| CAPSANTHIN | 6.640 | 26476 | 1523 | 1.73 | Fused |
| Unident0006 | 6.919 | 13869 | 2208 | 0.94 | Fused |
| Unident0007 | 7.025 | 47360 | 4396 | 3.22 | Fused |
| LUTEIN K1 | 7.900 | 0 | 0 | 0 | NF |
| ZEAXANTHIN | 8.000 | 0 | 0 | 0 | NF |
| RUBIXANTHIN | 8.550 | 0 | 0 | 0 | NF |
| CANTHAXANTHIN | 9.900 | 0 | 0 | 0 | NF |
| CITRAXANTHIN | 11.000 | 0 | 0 | 0 | NF |
| B CRYPTOXANTHIN | 12.792 | 48661 | 2698 | 3.31 | Fused |
| Unident0014 | 13.559 | 21569 | 873 | 1.47 | Fused |
| Unident0015 | 15.054 | 74757 | 2979 | 5.09 | Fused |
| LYCOPEEN | 16.096 | 46150 | 1463 | 3.14 | Fused |
| Unident0017 | 16.647 | 37968 | 1994 | 2.58 | Fused |
| Unident0018 | 17.747 | 28329 | 1296 | 1.93 | Fused |
| Unident0019 | 18.362 | 21985 | 1169 | 1.50 | Fused |
| B CAROTENE | 18.876 | 183451 | 8834 | 12.49 | Fused |
| Unident0021 | 19.526 | 21641 | 1410 | 1.47 | Fused |
| Unident0022 | 20.283 | 6424 | 585 | 0.44 | Resolved |
| Unident0023 | 23.517 | 45665 | 2343 | 3.11 | Fused |
| Unident0024 | 24.462 | 20179 | 669 | 1.37 | Fused |
| Unident0025 | 25.368 | 126787 | 5500 | 8.63 | Fused |
| Unident0026 | 26.136 | 66975 | 2185 | 4.56 | Fused |
| Unident0027 | 27.122 | 145853 | 6723 | 9.93 | Fused |
| Unident0028 | 27.882 | 70164 | 2310 | 4.78 | Fused |
| Unident0029 | 28.833 | 100228 | 4103 | 6.82 | Fused |
| Unident0030 | 29.594 | 40246 | 1614 | 2.74 | Fused |
| Unident0031 | 30.509 | 32888 | 1624 | 2.24 | Fused |
| Unident0032 | 30.732 | 35873 | 2197 | 2.44 | Fused |
| Unident0033 | 31.248 | 18710 | 891 | 1.27 | Fused |
| Unident0034 | 31.833 | 19004 | 1321 | 1.29 | Fused |
| Unident0035 | 32.239 | 17231 | 1315 | 1.17 | Fused |
| Unident0036 | 32.814 | 4583 | 399 | 0.31 | Fused |
| Unident0037 | 33.190 | 17009 | 1279 | 1.16 | Fused |
| Unident0038 | 33.604 | 5286 | 525 | 0.36 | Fused |
| Totals | | 1468907 | 75361 | 100.00 | |

Clearly, the untreated paprika has a large number of esters in the 23–25 area that are not present in the treated material. In both plant materials, whether treated or not, the capsanthin retains the high peak in the 6–7 range.

EXPERIMENT 5

CHICKEN TESTING OF THE PIGMENTATION EFFECT OF MARIGOLD MEAL PROCESSED IN SITU BY TRANSESTERIFICATION

Young Warren SEX-SAL-LINK hens were divided into three identical groups. Each group exists of 7 cages containing 3 hens each. The pullets had access to feed and water at all times.

The three groups were given the carrier feed (pigment free food) for 3 weeks as a control for the experiment.

Group A was fed ORO GLO®, a commercially available free form of lutein available from Kemin Industries, Inc., Des Moines, Iowa.

Group B will be fed the new invention made according to the process of EXPERIMENT 1 (7.5 mg of lutein activity per kg of feed).

Group C will be fed the new invention made according to the process of EXPERIMENT 1 (15.0 mg of lutein activity per kg of feed).

The experiment was run for 28 days. The feeding of the material requires 3 to 5 days before the effects on the yolk color are visible. Yolk color is uniform and consistent after approximately 21 days of feeding.

Ten (10) randomly chosen eggs laid by each group at day 0, 2, 4, 8, 16 and day 28 were broken; the egg yolk color was measured, and the total amount of feed intake was determined on the 28th day.

At days 0, 16 and day 28, the egg yolk of 3 randomly chosen eggs laid by each group had to be blended and weighed, followed by extraction and analysis of the egg yolk from each group.

Figure 5:
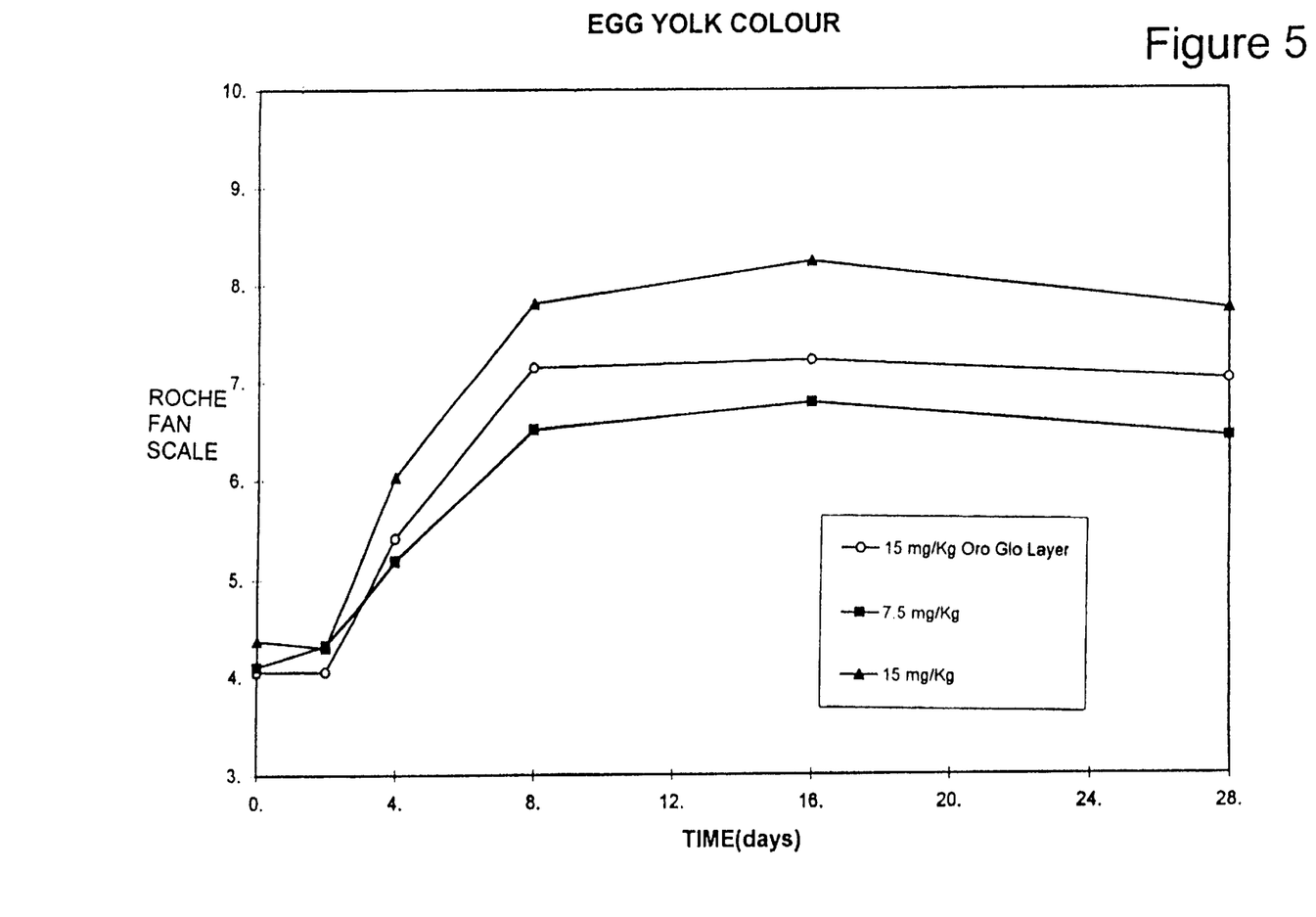
FIG. 5 is the Roche fan scale over days for the egg yolk color of the present invention at two mg/kg levels and of the commercial product.
Figure 6:
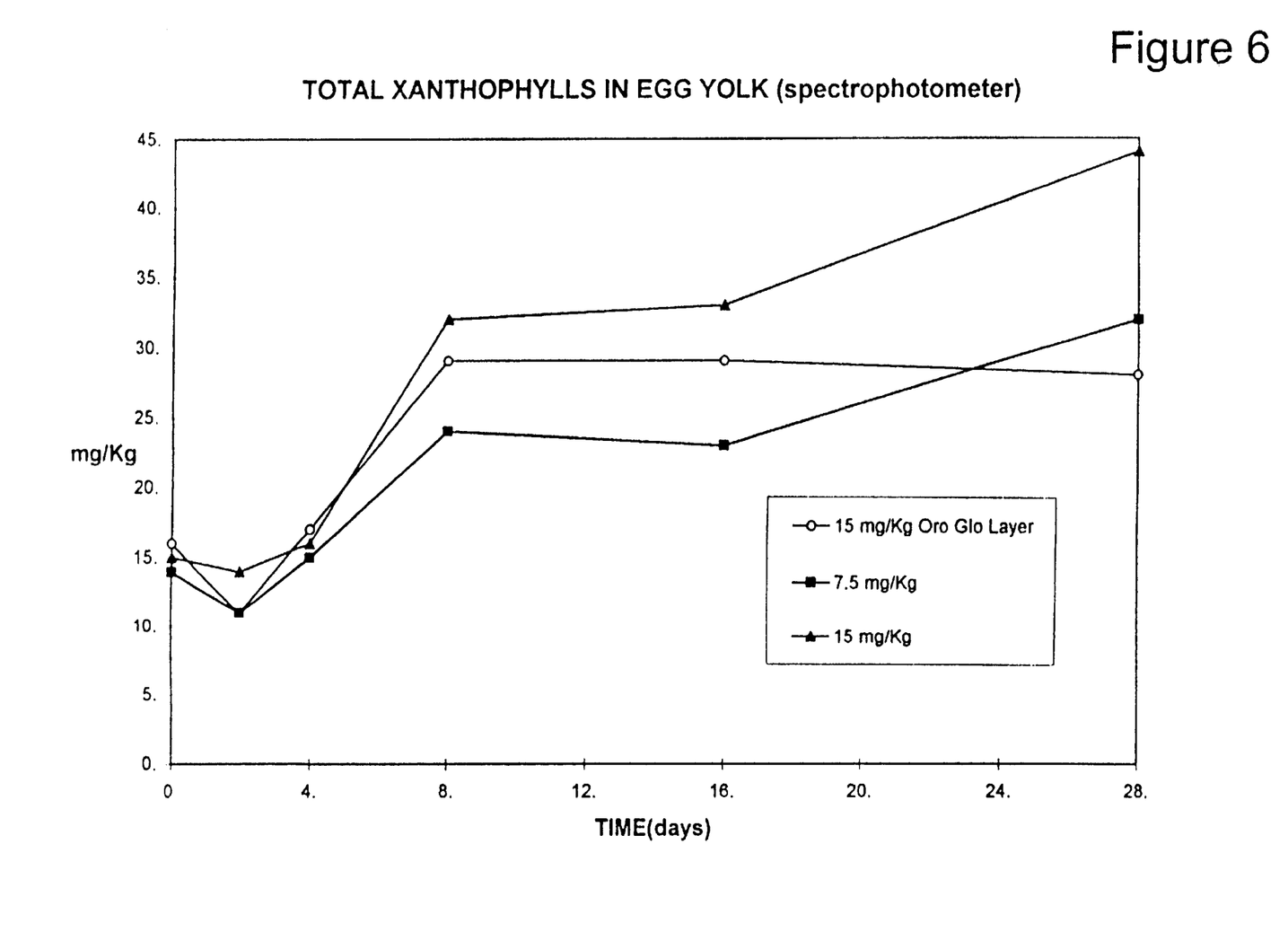
FIG. 6 is the mg/kg of xanthophylls in the egg yolks over days of the three treatments.

The relationship between the egg yolk color and the mg xanthophylls/kg of feed were calculated as well as the relationship between the amount of xanthophylls in the egg yolk and the xanthophylls fed. The results of this study are demonstrated in FIG. 5 and 6. FIG. 5 shows the Roche fan scale over days for the egg yolk color of the present invention and of the commercial product. FIG. 6 shows the mg/kg of xanthophylls in the egg yolks over days of the three treatments. The results show that the plant material is providing more pigment and color at the 15 mg level than is the commercial product. The 15 mg level appears to be a more effective level than the 7.5 mg level. The lower level is providing less egg yolk color, even though the egg appears to have more xanthophylls from the plant material in the egg yolk than the commercial product.

We claim:

1. A human food colorant composition comprising:

improved plant material containing in situ more free-form xanthophylls than the natural in situ amount of xanthophylls in the plant material from which the improved plant material was formed, wherein the xanthophylls are a natural food colorant, and wherein the improved plant material is made from a method of producing improved plant material made from a natural plant material containing at least some nonfree form xanthophylls, comprising the steps of:

treating said natural plant material in situ with a solvent, adding a base capable of transesterification of nonfree form xanthophylls to the free form xanthophylls, and, neutralizing the reaction wherein forming the improved plant material having more free forming xanthophylls than the natural plant material.

2. A human food colorant composition according to claim 1, wherein said improved plant material is flowers.

3. A human food colorant composition according to claim 2, wherein said flowers are marigolds.

4. A human food colorant composition according to claim 1, wherein said xanthophylls are lutein.

* * * * *